United States Patent [19]
Caruso

[11] 4,423,241
[45] Dec. 27, 1983

[54] HERBICIDAL COMPOSITION

[75] Inventor: Paul J. Caruso, Philadelphia, Pa.

[73] Assignee: Union Carbide Corporation, Danbury, Conn.

[21] Appl. No.: 367,017

[22] Filed: Apr. 9, 1982

Related U.S. Application Data

[63] Continuation of Ser. No. 192,703, Oct. 1, 1980, abandoned.

[51] Int. Cl.$^3$ ............................................. C07C 101/00
[52] U.S. Cl. ..................................... 560/35; 562/440; 564/164; 260/501.11; 260/465 E; 71/105; 71/111; 71/115; 71/118
[58] Field of Search ......................... 560/35; 562/440; 564/164; 260/501.11, 465 E; 71/111, 105, 115, 118

[56] References Cited

FOREIGN PATENT DOCUMENTS 46-7928  2/1971  Japan .................................... 562/440

OTHER PUBLICATIONS

Jan van Dijk et al., J. Med. Chem. 20 1199 (1977).

*Primary Examiner*—Paul J. Killos
*Attorney, Agent, or Firm*—D. L. Carlson; J. A. Shedden

[57] ABSTRACT

Novel 2,6-dihalogenated benzylidene aminooxyacetic acid compounds and derivatives thereof, have been found to have exceptional herbicidal activity, particularly in regard to nutsedge control.

12 Claims, No Drawings

HERBICIDAL COMPOSITION

This application is a continuation of our prior U.S. application: Ser. No. 192,703, filing date Oct. 1, 1980, abandoned.

FIELD OF THE INVENTION

The present invention relates generally to halogenated aromatic aminooxyacetic acid compounds and, more particularly, to certain 2,6-dihalobenzylideneaminooxyacetic acid compounds which have been found to have exceptional herbicidal activity.

BACKGROUND OF THE INVENTION

A major weed problem affecting large tracts of agronomic and horticultural lands is presented by nutsedge of both the yellow (*Cyperus esculentus*) and purple (*Cyperus rotundus*) variety. The plant grows from underground tubers which multiply in a radiated network from underground rhizome systems and also from seeds.

Certain nutsedge herbicides are known in the art. By way of illustration, U.S. Pat. No. 3,492,111 discloses 3-hydroxy-2,3',4'-trichloroacrylanilide as being particularly effective in the control of yellow nutsedge (*Cyperus esculentus*). However, there continues to be a commercial need for a nutsedge herbicide that is effective against purple, as well as yellow, nutsedge.

OBJECTS

It is an object of the present invention to provide a novel class of dihalogenated benzylidene aminooxyacetic acid compounds that has exceptional herbicidal activity.

It is another object of the invention to provide a novel herbicide that is particularly effective against yellow and purple nutsedge.

It is still another object of this invention to provide a novel herbicide that is effective as a broad-spectrum, pre-emergent total vegetative control agent.

These and other objects will become apparent from a reading of the detailed specification.

SUMMARY OF THE INVENTION

The present invention relates to novel 2,6-dihalobenzylideneaminooxyacetic acid compounds which have been found to have exceptional herbicidal activity. These compounds are particularly suitable for use as pre- and post- emergent nutsedge herbicides and can also be used as broad-spectrum, non-selective, total vegetative control pre-emergent herbicides. The compounds of the present invention have the following formula:

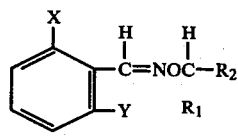

wherein X and Y are the same or different halogen; $R_1$ is hydrogen or C1 to C7 alkyl; and, $R_2$ is selected from the group consisting of a carboxyl group, a metal salt of a carboxyl group, a C1 to C12 ester of a carboxyl group, a C1 to C4 alkylamine salt of carboxyl group, an amide of a carboxyl group, a hydrazid of a carboxyl group, and a cyano group.

DESCRIPTION OF THE PREFERRED EMBODIMENTS

The preferred compounds within the scope of this invention are 2,6-dichlorobenzylideneaminooxyacetic acid, and salts or esters thereof. The term "ester of a carboxyl group" is intended to encompass alkyl esters, phenyl esters and thoiesters, either unsubstituted or substituted, and having the specified carbon limitation for the ester itself of from 1 to 12 carbons. If the ester is substituted, it can be substituted with substituents such as $C_1$ to $C_6$ alkyl, halo, amino, $C_1$ to $C_6$ alkylamino, nitro, cyano, $C_1$ to $C_6$ alkoxy, $CF_3$, and the like.

The term "metal salt" of a carboxyl group includes all metal salts such as sodium, potassium, calcium, lithium, magnesium, and the like.

The term "amide of a carboxyl group" includes unsubstituted amides or amides substituted with $C_1$ to $C_7$ alkoxy, $C_1$ to $C_{12}$ alkyl, halo, acetoxy, ($C_1$ to $C_{12}$ alkoxy) carbonyl ($C_1$ to $C_4$ alkyl), and the like.

The term "hydrazid of a carboxyl group" includes both unsubstituted hydrazids and hydrazids substituted with $C_1$ to $C_6$ alkyl, acetyl, phenyl (unsubstituted or substituted with nitro, halo, and the like), nitrophenyl, $C_1$ to $C_{12}$ alkoxycarbonyl $C_1$ to $C_4$ alkyl and the like.

The term halogen, as used herein, includes chlorine, bromine, iodine, and fluorine. The preferred halogens are bromine and chlorine, more preferably chlorine.

As stated above, the novel compounds useful in the process of the present invention are suitable for either pre- or post-emergent weed control applications. By "preemergence" is meant that the herbicidal compound is applied to the soil prior to emergence of the weed species sought to be controlled. This term, as used herein, also related to the application of herbicidal compound to areas where useful crops are to be grown but have not yet emerged from the soil.

By the term "postmergence" is meant that the herbicidal compound is applied to the plant sought to be controlled after it has emerged from the soil surface. The term, as used herein, also relates to the application of herbicidally active compounds to the soil surface at and around growing plants sought to be controlled for the purpose of effecting root adsorption of the compounds by the undesirable plant species.

The herbicidal compounds useful in the process of the present invention are produced by known methods. One such method involves the reaction of suitably substituted benzaldehyde with carboxymethoxylamine hemihydrochloride in aqueous/alcohol solution at a pH of between about 4 and about 6 at elevated temperature. The reactants in this method are made by known methods. For example, the carboxymethoxylamine hemihydrochloride reactant can be synethesized by the method disclosed in Organic Synthesis, Collective Volume III, p. 172 (1955). The benzaldehyde reactant can be prepared by the well-known procedure of hydrolyzing the corresponding benzal halide.

Another method of producing the herbicidal compounds useful in the present invention entails the reaction of the oxime of a suitably-substituted benzaldehyde with haloacetic acid (preferably bromacetic acid) in aqueous or alcoholic solvent at a basic pH.

The compounds useful in the present invention possess outstanding pre-and post-emergent herbicidal activity with respect to yellow and purple nutsedge, while having no significant adverse effects on many agronomic crops such as, for example, wheat, cotton, corn, peas, rice and peanuts. The instat compounds also exhibit excellent residual activity with respect to yellow and purple nutsedge weeks after treatment of soil containing nutsedge.

The instant compounds are preferably employed in an amount of from about 0.1 to about 1.5 lbs per acre when used as pre-emergent herbicides. As post-emergent herbicides, the compounds are preferably employed in an amount of from about 1.5 to about 4.0 lbs/acre, more preferably from about 3.0 to about 4.0 lbs/acre. Of course, the rates of application of the instant herbicides, either alone or in combination with one or more other herbicides, will vary depending on the nature of the soil, nature of the crops, extent of weed control desired, and the like. If total vegetation control is desired, rates of application of active compound in excess of 8 lbs/acre are preferred.

The compounds of this invention can conveniently be applied as pre-emergence herbicides in the form either of liquid or granular compositions, and can be either applied directly to the soil or incorporated into the soil before planting. The compounds are generally crystalline or oily materials with only slight solubility in water, so that where liquid formulations are desired they can be compounded in the form of wettable powders or emulsifiable concentrates which can be readily diluted with water prior to application. The compounds can also be applied in the form of herbicidal dusts, and may be combined with fertilizers or other herbicidal substances such as the N,N-dialkyl-thiol carbamates. Suitable granular compositions can readily be prepared by dissolving the herbicidal substance in a light organic solvent (such as acetone) and spraying the solution onto a carrier such as attapulgite, clay or vermiculite, the solvent then being removed by evaporation. Accordingly, this invention specifically provides for granular formulations of a novel compound of this invention together with a granular carrier material (which can, if desired also be a granular fertilizer material such as ammonium nitrate or urea prills). Suitable granular formulations are those containing from about 2 to 20% by weight of active ingredient uniformly dispersed on a dry granular carrier material such as attapulgite, clay, vermiculite or ground corn-cobs.

Salts of the acid compounds of the invention can generally be formulated by dissolving the salts in water, and stable salts within the scope of the invention constitute a preferred class of compounds.

Emulsifiable concentrates can be formulated by dissolving the herbicidal compound in an organic solvent (such as an aromatic oil which is readily dispersed in water), and if desired one or more co-solvents—such as the high alcohols or ketones, or butyrolactone can be used. Such concentrates are preferably formulated with wetting agents, and any suitable wetting agent, either anionic, cationic or nonionic may be employed.

Suitable surfactants are the known anionic or nonionic (particularly the latter) surfactants customarily employed in formulating herbicidal material. Examples of anionic surfactants are the sulphonates (such as the alkylbenzene sulphonates), the sulphated surfactants (such as sulphated alcohols, acids, amines, esters and sulfated natural fats and oils), and the phosphate esters (such as alkyl polyphosphate surfactants). Suitable nonionic materials include the polyoxyethylene surfactants (such as the ethoxylated alkyl phenols and the ethoxylated aliphatic alcohols) and the carboxylic esters (such as the poly-ethylene glycol esters and the polyoxyethylene fatty acid esters).

The novel compounds of this invention can, if desired, be used in combination with (or combined with) other known herbicides. In particular, combinations of 2,6-dichlorobenzylideneaminooxyacetic acid and EPTC (S-ethyl dipropyl thiocarbamate) have been found to be highly effective preferably as preplant soil incorporation treatments for potatoes. Thus, this invention specifically provides the use of the novel compounds, especially 2,6-dichlorobenzylideneaminooxyacetic acid in combination with one or more known herbicides such that for each part by weight of a novel compound there is also employed from about 0.25 to 4.0 parts by weight of a known herbicide (such as chloramben, EPTC and the like).

As noted above, the compounds and compositions of the instant invention may be utilized as preemergence herbicides, post-emergence herbicides and total vegetation control herbicides. One may utilize any prior art technique known to achieve the type of appliction desired such as, for example, incorporation in the soil, spraying, dusting, and the like.

The compounds contemplated in this invention may be applied as herbicides according to methods known to those skilled in the art. Herbicidal compositions containing the compounds as the active ingredient will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a non-phytotoxic solvent such as acetone xylene, and dispersing the active compound in water with the aid of suitable surface active emulsifying or dispersing agents, if needed.

The choice of dispersing and emulsifying agents and the amount employed is dictated by the nature of the composition and the ability of the agent to faciliate the dispersion o the herbicide. Generally, it is desirable to use as little of the agent as is possible, consistent with the desired dispersion of the herbicide in the spray so that rain does not re-emulsify the herbicide after it is applied to the plant and wash it off the plant. Nonionic, anionic, or cationic dispersing and emulsifying agents may be employed; for example, the condensation products of alkylene oxides with phenol and organic acids, alkyl aryl sulfonates, complex ether alcohols, quaternary ammonium compounds and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the herbicide contemplated herein may be applied per acre treated in from 1 to 200 gallons or more of liquid carrier and/or diluent in from about 5 to 500 pounds of inert solid carrier and/or diluent. The concentration in the liquid concentrate will usually vary from about 10 to 95 percent by weight and in the solid formulations from about 0.5 to about 90 percent weight. Satisfactory sprays, dusts, or granules for general use contain from about ¼ to 15 pounds of active herbicide per acre.

Typical compounds that can be used as herbicides in accordance with the present invention are the following:

2-bromo-6-fluorobenzylideneaminooxyacetic acid
2-bromo-6-iodobenzylideneaminooxyacetic acid
2-chloro-6-iodobenzylideneaminooxyacetic acid
2,6-dibromobenzylideneaminooxyacetic acid
2,6-dicyclobenzylideneaminooxyacetonitrile
n-octyl ester of 2,6-dichlorobenzylideneaminooxyacetic acid
phenyl ester of 2,6-dichlorobenzylideneaminooxyacetic acid
cyclohexyl ester of 2,6-dichlorobenzylideneaminooxyacetic acid
N-acetyl-$N^1$(2,6-dichlorobenzylideneaminooxyacetyl)hydrazine
N-cyanoacetyl-$N^1$(2,6-dichlorobenzylideneaminooxyacetyl)hydrazine
N-(2,6-dichlorobenzylideneaminooxyacetyl)-$N^1$-(2-hydroxyethyl)hydrazine
2,6-dichlorobenzylideneaminooxyacetamide
2,6-dichlorobenzylideneaminooxy-N-methylacetamide
2,6-dichlorobenzylideneaminooxy-N-ethylacetamide
2,6-dichlorobenzylideneaminooxy-N,N-diethylacetamide
2,6-dichlorobenzylideneaminooxy-N-methoxyacetamide
2,6-dichlorobenzylideneaminooxy-N-methoxy-N-methylacetamide
2,6-dichlorobenzylideneaminooxy-N-(3-methoxypropyl)acetamide
2,6-dichlorobenzylideneaminooxy-N-n-propylacetamide
2,6-dichlorobenzylideneaminooxy-N,N-di-n-propyacetamide
2,6-dichlorobenzylideneaminooxy-N-n-butyl-N-ethylacetamide
N-(2,6-dichlorobenzylideneaminooxyacetyl)aziridine
N-(2,6-dichlorobenzylideneaminooxyacetyl)pyrrolidine
N-(2,6-dichlorobenzlideneaminooxyacetyl)piperidine
N-(2,6-dichlorobenzylideneaminooxyacetyl)morpholine
N-(2,6-dichlorobenzylideneainooxyacetyl)glycine
ethylester of N-(2,6-dichlorobenzylideneaminooxyacetyl)glycine
N-(2,6-dichlorobenzylideneaminooxyacetyl)alanine
ethylester of N-(2,6-dichlorobenzylideneaminooxyacetyl)alanine
N-(2,6-dichlorobenzylideneaminooxyacetyl)glycineamide
N-2(2,6-dichlorobenzylideneaminooxyacetyl)proline
N-2(,2,6-dichlorobenzylideneaminooxyacetyl)glumatic acid
N-2(2,6-dichlorobenzylideneaminooxyacetyl)glutamine
N-(2,6-dichlorobenzylideneaminooxyacetyl)methionine
N-(2,6-dichlorobenzylideneaminooxyacetyl)hydrazine
N-(2,6-dichlorobenzylideneaminooxyacetyl)-$N^1,N^1$-dimethylhydrazine
N(2,6-dichlorobenzylideneaminooxyacetyl)-$N^1$-phenylhydrazine
N-(2,6-dichlorobenzylideneaminooxyacetyl)aminooxyacetic acid
ethylester of N-(2,6-dichlorobenzylideneaminooxyacetyl)aminooxyacetic acid As stated above, the herbicides of the present invention may be used alone or in admixture with known herbicides. A preferred class of known herbicides is those that are effective against weeds than other nutsedge, since a mixture of such known herbicides with the present compounds would be advantageous in agronomic areas where a nutsedge problem co-exists with other weed problems. If a mixture of herbicides is used, the mixture should be employed in a herbicidally effective amount. Examples of useful known herbicides include:

A. Benzo-2,1,3-thiadiazin-4-one-2,2-dioxides, e.g. those of formula:

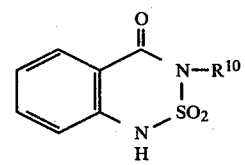

where $R^{10}$ is $C_1$-$C_6$ alkyl, in particular the compound in which $R^{10}$ is isopropyl, common name bentazon.

B. Hormone herbicides, particularly phenoxyalkanoic acids and their derivatives (salts, esters, amides and the like).
Examples of such acids are:
4-chloro-2-methylphenoxyacetic acid (common name MCPA)
2-(2,4dichlorophenoxy)propionic acid (common name dichloroprop)
2,4,5-trichlorophenoxyacetic acid (common name 2,4,5-T)
4-(4-chloro-2-methylphenoxy)butyric acid (common name MCPB)
2,4-dichlorophenoxyacetic acid (common name 2,4D)
4-(2,4-dichlorophenoxy)butyric acid (common name 2,4DB)
(2-(4-chloro-2-methylphenoxy)propionic acid (common name mecoprop)

C. 3-[4-(4-halophenoxy)phenyl]-1,1 dialkyl ureas, in particular the compound 3-[4-(4-chlorophenoxy)-phenyl]-1,1-dimethylurea (common name chloroxuron).

D. Dinitrophenols, for example those of formula:

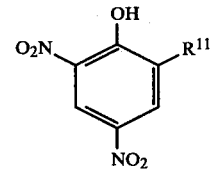

where $R^{11}$ is an alkyl group of 1 to 5 carbon atoms, and their derivatives, e.g. acetates; in particular such compounds wherein $R^{11}$ is methyl (common name DNOC), tert-butyl (common name dinoterb); or wherein $R^{11}$ is sec-butyl (common name dinoseb); and its ester dinoseb acetate.

E. Dinitroaniline herbicides, for example of formula:

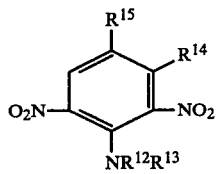

wherein $R^{12}$ is hydrogen or $C_1$–$C_6$ alkyl, cycloalkyl or alkenyl, optionally substituted with halogen. $R^{13}$ is $C_1$–$C_6$ alkyl; $R^{14}$ is hydrogen, methyl or chloro and $R^{15}$ is trifluoromethyl, $C_1$–$C_6$ alkyl, methyl sulphonyl or aminosulphonyl; in particular:

N'N'-diethyl-2,6-dinitro-4-trifluoromethyl-m-phenylenediamine (common name dinitramine)

2,6-dinitro-NN-dipropyl-4-trifluoromethylaniline (common name trifluralin)

4-methylsulphonyl-2,6-dinitro-NN-dipropylaniline (common name nitralin).

F. Phenylurea herbicides, e.g. of formula:

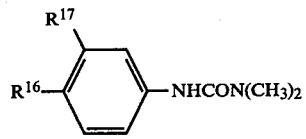

where $R^{16}$ and $R^{17}$ are independently hydrogen, chloro $C_1$–$C_4$ alkyl or alkoxy, or trifluoromethyl; in particular the compound in which $R^{16}$ and $R^{17}$ are both chloro (common name diuron), the compound in which $R^{16}$ is hydrogen and $R^{17}$ is trifluoromethyl (common name fluometuron).

G. Phenylcarbamoxyloxyphenylcarbamates, e.g. those of formula:

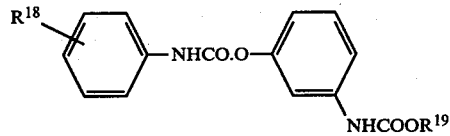

where $R^{18}$ is hydrogen or $C_1$–$C_4$ alkyl and $R^{19}$ is $C_1$–$C_4$ alkyl; in particular the compound where $R^{18}$ is m-methyl and $R^{19}$ is methyl (common name phenmedipham), and the compound where $R^{18}$ is hydrogen and $R^{19}$ is ethyl (common name desmedipham).

H. 2-phenylpyridazin-3-ones, e.g. those of formula:

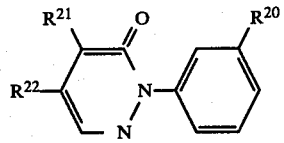

where $R^{20}$ is hydrogen or trifluoromethyl, $R^{21}$ is chloro, bromo or methoxy and $R^{22}$ is amino (optionally methyl substituted) or methoxy; particularly 5-amino-4-chloro-2-phenylpyridazine-3-one (common name pyrazon).

I. Uracil herbicides, for example of formula:

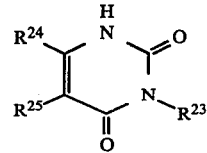

wherein $R^{23}$ is $C_3$–$C_5$ alkyl (preferably branched) or cyclohexyl, $R^{24}$ is methyl, $R^{25}$ is chlorine or bromine; or $R^{24}$ and $R^{25}$ together represent a $C_3$–$C_4$ alkylene bridge, particularly:

3-cyclohexyl-5,6-trimethylene uracil (common name lenacil)

5-bromo-3-sec-butyl-6-methyluracil (common name bromacil)

3-tert-butyl-5-chloro-6-methyluracil (common name terbacil)

J. Triazine herbicides, for example of formula:

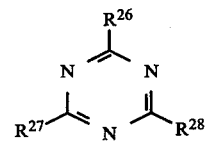

wherein $R^{26}$ is chloro, methoxy, methylthio or ethylthio; $R^{27}$ is ($C_1$–$C_6$) alkylamino alkoxyalkylamino or dialkylamino; and $R^{28}$ is ($C_1$–$C_6$) alkylamino alkoxyalkylamino, cyanoalkylamino, dialkylamino or azido; particularly:

2-chloro-4-ethylamino-6-isopropylamino-1,3,5-triazine (common name atrazine)

2-chloro-4,6-di(ethylamino)-1,3,5-triazine (common name simazine)

2-azido-4-isopropylamino-t-methylthio-1,3,5-triazine (common name aziprotryne)

1-alkoxy-1-alkyl-3-phenylurea herbicides, e.g. of formula:

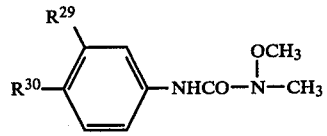

wherein $R^{29}$ is hydrogen or chloro and $R^{30}$ is chloro, bromo or ethoxy; in particular;

3-(3,4-dichlorophenyl)-1-methoxyl-1-methylurea (common name linuron)

3-(4-chlorophenyl)-1-methoxyl-1-methylurea (common name monolinuron)

3(4-bromo-4-chlorophenyl)-1-methoxy-1-methylureau (common name chlorobromuron)

L. Thiolcarbamate herbicides such as S-propyl dipropyl-thiocarbamate (common name vernolate).

M. 1,2,4-Triazine-5-one herbicides, e.g. of formula:

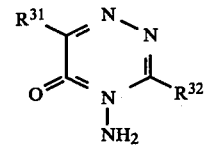

where $R^{31}$ is $C_3$-$C_6$ alkyl or cycloalkyl, or phenyl; and $R^{32}$ is methyl or methylthio; in particular:
4-amino-4,5-dihydro-3-methyl-6-phenyl-1,2,4-triazine-5-one (common name metamitron)
4-amino-6-tert-butyl-4,5-dihydro-3-methylthio-1,2,4-triazine-5-one (common name metribuzin).

N. Benzoic acid herbicides, e.g. those of formula:

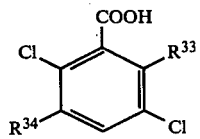

wherein $R^{33}$ is hydrogen, chloro or methoxy and $R^{34}$ is hydrogen or amino; especially 2,3,6-trichlorobenzoic acid (common name 2,3,6-TBA) 3,6-dichloro-2-methoxybenzoic acid (common name dicamba) and 3-amino-2,5-dichlorobenzoic acid (common name chloramben).

O. Anilide herbicides, e.g. those of formula:

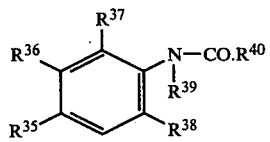

where $R^{35}$ and $R^{36}$ are hydrogen, chloro or methyl; $R^{37}$ and $R^{38}$ are H, methyl or ethyl; $R^{39}$ is hydrogen, $C_1$-$C_4$ alkyl or alkynyl, optionally substituted with $C_1$-$C_4$ alkoxy or ethoxycarbonyl; and $R^{40}$ and $C_1$-$C_6$ alkyl, cycloalkyl or alkenyl, optionally chloro-substituted; particularly N-butoxymethyl-α-chloro-2',6'-diethylacetanilide (common name butachlor); the corresponding N-methoxy compound (common name alachlor); the corresponding N-isopropyl compound (common name propachlor) and 3'4'dichloropropionanilide (common name propanil).

P. Dihalobenzonitrile herbicides: for example, 2,6-dichlorobenzonitrile (common name dichlobenil; 3,5-dibromo-4-hydroxybenzonitrile (common name bromoxynil) and 3,5-diiodo-4-hydroxybenzonitrile (common name ioxynil)

Q. Haloalkanoic herbicides, e.g. 2,2-dichloropionic acid (common name dalapon). trichloroacetic acid (common name TCA) and salts thereof.

R. Diphenylether herbicides, e.g. 4-nitrophenyl 2'-nitro-4-trifluoromethyl phenyl ether (common name fluorodifen); methyl-5-(2,4-dichlorophenoxy)-2-nitrobenzoate (common name bifenox) 2-nitro-5-(2-chloro-4-trifluoromethylphenoxy) benzoic acid; and 2-chlorophenyl-3'-ethoxy-4'-nitro-4-trifluoromethyl phenyl ether.

S. Miscellaneous herbicides includes N,N-dimethyldiphenylacetamide (common name diphenamid); N-1-naphthylphthalamic acid (common name naptalam) and 3-amino-1,2,4-triazole.

Mixtures of the above known herbicides with herbicides of the present invention can be used to treat a wide variety of crops.

The following examples are intended to illustrate, but in no way limit, the present invention.

Example 1—Preparation and Testing of Instant Herbicides (A) (Compound A)

Preparation of 2,6-Dichlorobenzylideneaminooxyacetic acid

To a solution of 11.5 gm. (0.105 equivalents) of carboxymethoxylamine hemihydrochloride and 12.2 gm. (0.149 equivs.) of anhydrous sodium acetate ... or 20.2 gm. of sodium acetate trihydrate ... in 300 ml. of water there was added, with stirring, a warm solution of 17.5 gm. (0.100 mole) of 2,6-dichlorobenzaldehyde in 300 ml. of ethanol. Stirring was continued while heating the reaction mixture on the steam bath for an hour, after which it was evaporated to one-half volume. The cooled mixture was then adjusted to pH 8-9 with cold, aqueous sodium carbonate and was then freed of non-acidic contaminants by either extraction. The aqueous-alkaline phase, cooled in ice bath, was adjusted to pH 1-2 by stirring in concentrated hydrochloric acid. The product which separated was removed by filtration, washed with cold water and dried at room temperature to obtain 23.9 gm. (96.3%) of colorless, crystalline product melting at 177°-9° C. Recrystallization from aqueous alcohol gave material melting at 178.5°-179.0° C. (uncorrected).

Calc'd. for $C_9H_7ClNO_3$: C, 43.6: H, 2.8: Cl, 28.6: N, 5.65; Found: C, 43.7; H, 2.9; Cl, 28.6; N, 5.6.

(B)

Preparation of 2,6-Dichlorobenzylideneaminooxyacetic Acid, Methyl Ester (Compound B)

A mixture of 12.4 gm. (0.050 mole) of 2,6-dichlorobenzylideneaminooxyacetic acid, 4.8 gm. (0.150 mole) of methanol and about 0.8 gm. of methanesulfonic acid in 15 ml. of 1,2-dichloroethane was refluxed for 15-16 hours. The cooled reaction mixture was then washed with cold, aqueous sodium bicarbonate, followed by a cold water wash. The organic phase was then concentrated under reduced pressure and at a mixture bath temperature of about 60° C. The resulting oil solidified on cooling. There were obtained 12.5 gm. (96%) of product melting at 58°-65° C. Purification by high vacuum distillation yielded material which, when allowed to crystallize, melted at 60°-62° C. (uncorrected).

Calc'd. for $C_{10}H_9Cl_2NO_3$: C, 45.8; H, 3.5; Cl, 27.05; N, 5.3; Found: C, 45.8; H, 3.5; Cl, 27.15; N, 5.3.

(C)

Preparation of 2,6-Dichlorobenzylideneaminooxy-N,N-dimethylacetamide (Compound C)

To an ice-cold solution of 5.7 gm. (0.126 mole) of dimethylamine in 100 ml. of methanol there were added 3.3 gm. (0.0126 mole) of the methyl ester of 2,6-dichlorobenzylideneaminooxyacetic acid. The reaction mixture was stirred at ice bath temperature for about two hours; a reflux condenser sealed with a thin rubber diaphragm was then attached to the reaction vessel, and the reaction mixture was then allowed to warm spontaneously to room temperature. The sealed system was left at room temperature for several days; it was then heated on the steam bath for one-half hour. Concentration of the reaction mixture under reduced pressure left 3.4 gm. of crude product. A product melting at 90.5°-91.5° C. was obtained by a recrystallization from aqueous-alcohol, followed by chromatographing on a silica gel column with ethyl acetate.

Calc'd. for $C_{11}H_{12}Cl_2N_2O_2$: C, 48.0; H, 4.4; Cl, 25.8; N, 10.2; Found: C, 48.2; H, 4.7; Cl, 25.7; N, 10.1.

(D) (Compound D)

Preparation of 2,6-Dichlorobenzylideneaminooxyacetyl Chloride

A mixture of 12.4 gm. (0.05 mole) of 2,6-dichlorobenzylideneaminooxyacetic acid and 18 gm. (0.15 mole) of thionyl chloride in 100 ml. of methylene chloride was refluxed for eight hours, after which the bulk of the methylene chloride and excess thionyl chloride were removed by distillation from the steambath. There was then added 200 ml. of n-heptane and distillation was resumed to strip off any remaining thionyl chloride and the bulk of the n-heptane. An additional 100 ml. of n-heptane was then added, the mixture was heated and was filtered through a ¼ inch-deep bed of filter-aid. The filtrate was then stirred, in a system protected from atmospheric moisture by a drying tube, while chilling in a Dry Ice/alcohol bath. The crystalline solid which separated was removed by filtration, washed on the filter with cold n-hexane and dried in vacuum dessicator over $P_2O_5$ to obtain 7.3 gm. of 2,6-dichlorobenzylideneaminooxyacetyl chloride, melting at 46°–50° C. An additional 3.4 gm. of somewhat lower-melting product was obtained by concentrating and chilling the mother liquors, bringing the overall yield of material to about 80% of theory. This material was used without further purification.

(E) (Compound E)

Preparation of 2,6-Dichlorobenzylideneaminooxyacetamide

A solution of 3.2 gm. (0.012 mole) of 2,6-dichlorobenzylideneaminooxyacetyl chloride in 60 ml. of methylene chloride was added in small portions to 60 ml. of stirred, ice-cold, 28% aqueous ammonia. Stirring was then continued, first at ice-bath temperature for an hour, then at room temperature for several hours. The reaction mixture was then distilled under reduced pressure until all of the methylene chloride was removed. The remaining aqueous suspension was then cooled in ice bath, was filtered, and the product on the filter was washed with cold water. The dried product weighed 2.7 gm. (91%). Consecutive recrystallizations from aqueousmethanol, then from isopropyl alcohol/n-heptane yielded 1.5 gm. of 2,6-dichlorobenzylideneaminooxyacetamide melting at 122°–4° C.

(F) (Compound F)

Preparation of 2,6-Dichlorobenzylideneaminooxy-N-methoxyacetamide

A mixture of 1.8 gm. (0.022 mole) of methoxyamine hydrochloride and 5.3 gm. (0.065 mole) of anhydrous sodium acetate in 100 ml. of methanol was stirred in a vessel immersed in a water bath at room temperature. To the above was added, dropwise and with continuous stirring, a solution of 2.4 gm. (0.0090 mole) of 2,6-dichlorobenzylideneaminooxyacetyl chloride in 30 ml. of toluene. Stirring at room temperature was then continued for an hour, after which the reaction mixture was heated for 1½ hours on the steam bath. The mixture was then filtered hot, washing the filter-cake with hot methanol. The combined filtrates were evaporated to dryness; the residue was taken up in ether, washed with water, and the ether removed under reduced pressure. The residue was chromatographed on a silica gel column using n-heptane/ethyl acetate as the eluting solvent. There were obtained 2.0 gm. of 2,6-dichlorobenzylideneaminooxy-N-methoxyacetamide melting at 72.0°–74.5° C.

(G)

Preparation of 2,6-Dichlorobenzylideneaminooxy-N-methoxy-N-methylacetamide (Compound G)

A mixture of 3.0 gm. (0.031 mole) of N,O-dimethylhydroxylamine hydrochloride and 60 ml. of methanol was cooled in ice bath; then 6.3 gm. (0.062 mole) of triethylamine was stirred in. A solution of 4.1 gm. (0.015 mole) of 2,6-dichlorobenzylideneaminooxyacetyl chloride in toluene was added dropwise and with cooling and stirring. After one hour more at ice-bath temperature the reaction mixture was allowed to stand overnight at room temperature; then evaporate to dryness under reduced pressure. The residue was ground under water, separated, extracted with methylene chloride, and the extract was treated with decolorizing carbon, then filtered. The filtrate, evaporated to dryness under reduced pressure, gave 3.1 gm. (69.1%) of a solid melting at 62°–72° C. The melt was turbid, however, and the crude product was extracted with hot n-heptane. The hot extract was passed through a Florisil* column; evaporation of the solvent left product melting at 76°–78° C. (clear).

(H)

Preparation of 4-Cyano-2,6-dibromophenyl 2,6-dichlorobenzylideneaminooxyacetate (Compound H)

A mixture of 2.1 gm. (0.0076 mole) of 4-cyano-2,6-dibromophenol (m.p. 190.0°–191.5° C.), 40 ml. of toluene and 0.8 gm. (0.008 mole) of triethylamine was stirred in a system protected from atmospheric moisture by a 'drying tube', and to it there were added, in portions, a total of 2.0 grams (0.0075 mole) of 2,6-dichlorobenzylideneaminooxyacetyl chloride. The reaction mixture was then heated for an hour on the steambath; it was filtered hot, washing the triethylamine hydrochloride on the filter with hot toluene, then discarding it. The combined filtrates were evaporated to dryness under reduced pressure, and the residue was triturated with cold methanol, then filtered. The filter-cake was then washed with cold methanol and air-dried to obtain 3.3 gm. (85.6%) of colorless solid, m.p. 166°–168° C. This material was treated with boiling isopropyl alcohol and n-heptane mixture, and was then cooled in ice bath. The solid present was removed by filration, washed on the filter with n-hexane and dried in air to obtain 3.1 gm. of crystalline product melting at 168.0°–170.5° C. (uncorrected).

(I)

Preparation of 2,6-Dichlorobenzylideneaminooxy-N,N-dimethylacethydrazide (Compound I)

A solution of 2.0 gm. (0.033 mole) of N,N-dimethylhydrazine in 10 ml. of peroxide-free, anhydrous ether was added dropwise to a solution, at 35°–40° C., of 3.2 gm. (0.012 mole) of 2,6-dichlorobenzylideneaminooxyacetyl chloride in a mixture of 40 ml. each of n-heptane and methylene chloride in a system protected from atmospheric moisture. Stirring at 35°–40° C. was maintained for an hour; the reaction mixture was then transferred to a separatory funnel with the volumes of methylene chloride and was washed with several portions of cold water. The organic phase was then evaporated under reduced pressure to obtain 3.7 gm. of amber-colored, viscous material which slowly crystallized at room temperature. It was recrystallized from isopropyl alcohol and hexane to give 2.1 gm. of product melting from 89.5°–91.5° C.

(J) (Compound J)

Preparation of N-(2,6-Dichlorobenzylideneaminooxyacetyl)glycine

A solution of 3.1 gm. (0.012 mole) of 2,6-dichlorobenzylideneaminooxyacetyl chloride in toluene was added dropwise to a stirred mixture of 0.9 gm. (0.012 mole) of glycine and 2.4 gm. (0.024 mole) of triethylamine in 60 ml. of dry methanol at room temperature. The reaction mixture was allowed to stand for two days, at room temperature, and was then evaporated under reduced pressure up to maximum pot temperature 70°–80° C. The residue was triturated with water, and the mixture was adjusted to pH 1.5 with hydrochloric acid, stirring for several minutes longer. The slightly gummy solid obtained was stirred thoroughly with 80 ml. of 50% aqueous ethanol at 50° C.; the mixture was then allowed to stand at room temperature, in an open beaker, overnight. The practically colorless material was removed by filtration, was washed with cold aqueous-alcohol, and was dried to obtain 1.3 gm. of product melting, with decomposition, at 192°–194° C.

(K)

Preparation of N'-Acetyl-N-(2,6-dichlorobenzylideneaminooxyaceto)-hydrazide (Compound K)

A mixture of 0.90 gm. (0.012 mole) of dry acetohydrazide and 1.3 gm. (0.013 mole) of triethylamine in 50 ml. of dry methanol was stirred at room temperature in a system protected from atmospheric moisture. A solution of 3.0 gm. (0.011 mole) of 2,6-dichlorobenzylideneaminooxyacetyl chloride in toluene was added in small portions, after which the reaction mixture was heated under reflux on the steam bath for an hour. Evaporation under reduced pressure left a residue which, after trituration with water, was air-dried to obtain 3.0 gm. (87.3%) of material melting at 167°–172° C. Recrystallization from aqueous-methanol yielded colorless product melting at 172.5°–173.5° C.

(L)

Preparation of 2,6-Dichloro-3-nitrobenzylideneaminooxyacetic Acid (Comparative Compound L)

A warm solution of 2,6-dichloro-3-nitrobenzaldehyde, 1.8 gm. in 20 ml. of ethanol was stirred into a solution of 0.9 gm. (0.008 equivs.) of carboxymethoxylamine hemihydrochloride and 0.45 gm. of sodium acetate, anhyd., in 20 ml. of water at room temperature. The mixture was heated on the steam bath for one-half hour, and was then evaporated to dryness at room temperature. The residue was triturated with cold water, filtered, washed with cold water and dried in air to obtain 2.1 gm. (87.4%) of crude material melting at 76°–84° C. This was purified from aqueous-methanol to obtain 1.9 gm. of pale cream-colored product melting at 82°–85° C.

(M) (Comparative Compound M)

Preparation of 2,3,6-Trichlorobenzylideneaminooxyacetic Acid

A warm solution of 3.0 gm. (0.014 mole) of 2,3,6-trichlorobenzaldehyde in 50 ml. of ethanol was stirred into a warm solution of 1.6 gm. (0.015 equiv.) of carboxymethoxylamine hemihydrochloride and 0.7 gm. (0.008 mole) of anhyd. sodium acetate in 50 ml. water. Heating on the steam bath was maintained for one-half hour: then the reaction mixture was evaporated by 3/4 volume and was cooled. The solid present was removed by filtration, washed with water and dried in vacuum dessicator over phosphorus pentoxide to obtain 3.9 gm. (96.5%) of crude product melting at 159°–160° C. This material, twice recrystallized from aqueous-isopropyl alcohol, melted at 160°–161° C.

Calc'd. for $C_9H_6Cl_3NO_3$: C, 38.26; H, 2.14; Cl, 37.65; N, 4.96; Found: C, 38.45; H, 2.14; Cl, 37.49; N, 4.98.

(N) (Comparative Compound N)

Preparation of 2-Chloro-6-nitrobenzylideneaminooxyacetic Acid

A warm solution of 2.5 gm. (0.014 mole) of 2-chloro-6-nitrobenzaldehyde in 40 ml. of alcohol 3A was added, with stirring, to a warm solution of 1.5 gm. (0.014 equivs.) of carboxymethoxylamine hemihydrochloride and 1.7 gm. (0.021 equiv.) of anhyd. sodium acetate in 40 ml. of water. The reaction mixture was heated a half-hour on the steam bath, and was then evaporated to a volume of about 20 ml. A solid separated upon cooling; it was filtered from the mixture, washed with cold water and dried in air to give 2.7 gm. (77.3%) of tan-yellow colored material melting at 136°–141° C. Recrystallization from n-hexane/isopropyl alcohol yield 2.5 gm. of pale tan-yellow crystalline product melting at 144°–146° C.

(O) (Compound O)

Preparation of 2-Chloro-6-fluorobenzylideneaminooxyacetic Acid

A warm solution of 2.0 gm. (0.013 mole) of 2-chloro-6-fluorobenzaldehyde in 40 ml. of ethanol was stirred into a warm solution of 1.4 gm. (0.013 equiv.) of carboxymethoxylamine hemihydrochloride and 0.6 gm. (0.007 mole) of anhyd. sodium acetate in 40 ml. of water. The mixture was heated a half-hour on the steam bath, and was then evaporated to dryness under reduced pressure to yield an oil, which was induced to crystallize by vigorous stirring. The solid material was triturated under water, removed by filtration, washed with water and dried in air to obtain 2.7 gm. (92.5%) of crude product melting from 95°–115° C. Recrystallization from n-heptaine/isopropyl alcohol gave 2.0 gm. of product melting at 116°–118° C.

(P)

Preparation of (±)2-(2-Chloro-6-fluorobenzylideneaminooxy)propionic acid (Compound P)

A warm solution of 4.0 gm. (0.025 mole) of 2-chloro-6-fluorobenzaldehyde in 50 ml. of ethanol was stirred into a solution of 3.1 gm. (0.025 equiv.) of (±)2-aminooxypropionic acid hemihydrochloride and 2.1 gm. (0.026 equivs.) of anhyd. sodium acetate in 50 ml. water. After heating one-half hour on steam bath, the reaction mixture was evaporated to dryness and the residue was washed with water and dried in dessicator over $P_2O_5$. There were obtained 5.3 gm. of crude product melting at 98°–102° C. Recrystallization from isopropyl alcohol and n-heptane to obtain product melting at 105.5°–107.0° C.

(Q) (Comparative Compound Q)

Preparation of
2-Chloro-6-methylbenzylideneaminooxyacetic Acid

A warm solution of 1.5 gm. (0.01 mole) of 6-chloro-o-tolualdehyde in 15 ml. of ethanol was stirred into a solution of 1.1 gm. (0.010 equiv.) of carboxymethoxylamine hemihydrochloride and 1.3 gm. (0.016 equivs.) of anhyd. sodium acetate in 15 ml. water. After heating a half hour on the steam bath, the reaction mixture was cooled and adjusted to pH 8 with 5% aqueous sodium hydroxide. The mixture was extracted with ether, and the ether extract was discarded. The alkaline-aqueous phase was then adjusted to pH 5 with hydrochloric acid and was evaporated to 25 ml. volume. It was then acidified to pH 1.5–2.0 with cooling in ice bath. The solid was removed by filtration, was washed with cold water, and was dried in air to obtain 1.5 gm. (68%) of crude product melting at 121°–6° C. Recrystallization from aqueous-ethanol yielded 1.4 gm. of product melting at 124°–7° C. (dried at 65° C. in vacuo).

(R)

Preparation of Ethanolamine Salt of
2,6-Dichlorobenzylideneaminooxyacetic Acid
(Compound R)

A stirred suspension of 3.7 gm. (0.015 mole) of 2,6-dichlorobenzylideneaminooxyacetic acid in 100 ml. of water at room temperature was treated with an equivalent amount of ethanolamine. After a sufficient period of stirring, to solubilize the solid, the mixture was filtered, to removed any remaining turbidity, and the clear filtrate was evaporated to near-dryness under reduced pressure. The residual material was then freed of any remaining water by azeotropic distillation with suitable solvent. The dry, residual mixture was then evaporated to dryness under reduced pressure to obtain the product, a colorless, waxy, somewhat hygroscopic material. I.R. spectrum confirms salt structure. An aqueous solution of the product had pH ~5.

(S) (Compound S)

Preparation of
2,6-Dichlorobenzylideneaminooxyacetronitrile

A mixture of 4.1 gm. (0.016 mole) of 2,6-dichlorobenzylideneaminooxyacetamide, 3 m. of dry toluene and 1.8 ml. of "purified" thionyl chloride was stirred and refluxed, in a system protected from atmospheric moisture, for about an hour. The reaction mixture was transferred, with the aid of toluene, to a beaker containing crushed ice. The stirred mixture was then carefully adjusted to pH 6–8, and the organic phase was treated with decolorizing carbon and filtered. The filtrate was evaporated to small volume, and was chromatographed on a silicic acid column using 1:1 toluene-cyclohexane solvent system. There were obtained 1.2 gm. of pale yellow solid melting at 45°–9° C. This was recrystallized from reagent-grade isooctane to obtain 1.0 gm. of product melting at 49.5°–51.0° C. A sample dried in vacuo at ambient temperature was sent for elemental analysis:

Calculated for $C_9H_6Cl_2N_2O$: C,47.2; H,2.6; Cl,31.0; N,12,2. Found: C,47.4; H,2.6; C,31.1; H,12.4.

Testing

Compounds, identified by letters specified in the preparation section above, were tested under greenhouse conditions at a rate of 8 lbs./acre of compound for percent yellow nutsedge control under both pre-emergence and post-emergence conditions. Comparisons were made against three comparative examples (compounds N, L and Q) and a control which provided zero percent nutsedge control both pre-emergent and post-emergent. The results, in terms of percent nutsedge control, are given in Table I which follows:

TABLE I

| | Percent Yellow Nutsedge Control at 8 lbs./acre | |
|---|---|---|
| Compound | Pre-emergent | Post-emergent |
| A | 100 | 100 |
| O | 100 | 10 |
| P | 100 | 0 |
| M | 40 | 0 |
| N | 0 | 0 |
| L | 0 | 0 |
| Q | 0 | 0 |
| B | 100 | 100 |
| H | 20 | 0 |
| G | 100 | 30 |
| E | 100 | 60 |
| C | 100 | 0 |
| F | 100 | 0 |
| K | 100 | 50 |
| I | 100 | 30 |
| J | 100 | 0 |

Example 2—Testing of Compounds on Various Weeds

Several compounds, identified by the letters given in th preparation section of Example 1 above, were tested under greenhouse conditions at 8 lbs./acre of compound on various weed species as given in Table II. Compounds of the invention (A, B and E) were compared against a comparison compound (M). The results, in terms of percent weed control, are given in Table II which follows:

TABLE II

Pre- and Post-Emergent Testing of Certain Compounds Prepared in Example 1 at 8 lbs./Acre for Various Weeds, Percent Control

| Species of Plant Weeds | Compound A | | Compound B | | Compound E | | Compound M | |
|---|---|---|---|---|---|---|---|---|
| | Pre | Post | Pre | Post | Pre | Post | Pre | Post |
| 1. Barnyard | 90 | 10 | 30 | 10 | 100 | 0 | 15 | 15 |
| 2. Sorghum | 30 | 10 | 20 | 0 | 20 | 0 | 0 | 0 |
| 3. Downy-brome | 100 | 60 | 100 | 30 | 100 | 30 | 10 | 0 |
| 4. Wild Oats | 100 | 80 | 100 | 50 | 100 | 60 | 15 | 0 |
| 5. Crabgrass | 95 | 10 | 20 | 50 | 35 | 0 | 0 | 10 |
| 6. Foxtail | 80 | — | 100 | 40 | 60 | 40 | 0 | 0 |
| 7. Wild Mustard | 50 | 30 | 100 | 100 | 100 | 25 | 50 | 50 |
| 8. Teaweed | 100 | 40 | 100 | 100 | 100 | 10 | 10 | 30 |
| 9. Cucumber | 50 | 70 | 100 | 90 | 100 | 20 | 100 | 0 |
| 10. Velvet Leaf | 100 | 30 | 100 | 10 | 100 | 15 | 20 | 20 |
| 11. Marigold | 100 | 50 | 100 | 25 | 100 | 15 | 20 | 20 |
| 12. Flax | 100 | 25 | 100 | 10 | 100 | 0 | 10 | 25 |
| 13. Black Nightshade | 100 | 30 | 100 | 100 | 100 | 60 | 30 | 10 |
| 14. Morning-glory | 70 | 50 | 100 | 60 | 100 | 25 | 25 | 50 |
| 15. Yellow Nutsedge | 100 | 100 | 100 | 100 | 100 | 60 | 50 | 0 |

TABLE II-continued

Pre- and Post-Emergent Testing of Certain
Compounds Prepared in Example 1 at
8 lbs./Acre for Various Weeds,
Percent Control

| Species of Plant Weeds | Compound A | | Compound B | | Compound E | | Compound M | |
|---|---|---|---|---|---|---|---|---|
| | Pre | Post | Pre | Post | Pre | Post | Pre | Post |
| 16. Snapbeans | 50 | 60 | 100 | 70 | 100 | 70 | 30 | 40 |

Example 3

Preemergence application of 2,6-dichlorobenzylidineaminooxyacetic acid (Example 3) was made at rates of 2 and 4 lbs./acre under greenhouse conditions to soil freshly seeded with yellow or purple nutsedge tubers, as specified in Table III below. For purposes of comparing the herbicidal effectiveness of certain well-known prior art compounds, identical amounts of these compounds, include the preferred compound disclosed in U.S. Pat. No. 3,492,111 namely 3-hydroxy-2,3',4'-trichloroacrylanilide (comparison A) and bentazon in the form of BASAGRAN, a product of BASF Corporation (Comparison B), under analogous greenhouse conditions.

Results, as reported in Table III below, were obtained at time period ranging from two weeks after application of compound to the soil surface in the case of bentazon, to four weeks after application in the case of 2,6-dichlorobenzylidineaminooxyacetic acid, and six seeks after application in the case of 3-hydroxy-2,3',4'-trichloroacrylanilide.

TABLE III

PRE-EMERGENT APPLICATION -
PERCENT CONTROL OF NUTSEDGE

| | Yellow nutsedge, percent control | | | Purple nutsedge, percent control | | |
|---|---|---|---|---|---|---|
| | Example 3[1] | Comparison A[2] | Comparison B[3] | Example 3[1] | Comparison A[2] | Comparison B[3] |
| 2 lbs./acre | 100 | 100 | NR[4] | 100 | 0 | NR[4] |
| 4 lbs/acre | 100 | 100 | 60 | 100 | 0 | 15 |

[1]Example using 2,6-dichlorobenzylidineaminooxyacetic acid.
[2]Comparative example using 3-hydroxy-2,3',4',-trichloroacrylanilide
[3]Comparative example using BASAGRAN
[4]"NR" denotes "not run".

Example 4

Postemergence applications of 2,6-dichlorobenzylidineaminooxyacetic acid (Example 4) was made at rates of 2 and 4 lbs./acre under greenhouse conditions to soil containing yellow or purple nutsedge plants, as specified in Table IV, growing in four inch pots. At the time of spray application, which was effected using water/alcohol solutions of the respective active ingredients, the nutsedge plants were in an active state of growth as evidenced by tillering and the formation of tubers. Comparison under analogous greenhouse conditions was made against 3-hydroxy-1,3',4'-trichloroacrylanilide (Comparison C) and bentazon in the form of BASAGRAN (Comparison D).

Results, as given in Table IV below, were obtained at time periods ranging from two weeks after application of compounds to the nutsedge plants in the case bentazon, to four weeks after application in the case of 2,6-dichlorobenzylidineaminooxyacetic acid, and six weeks after application in the case of 3-hydroxy-2,3',4'-trichloroacrylanilide.

TABLE IV

POST EMERGENT APPLICATION -
PERCENT CONTROL OF NUTSEDGE

| | Yellow nutsedge, percent control | | | Purple nutsedge, percent control | | |
|---|---|---|---|---|---|---|
| | Example 4[1] | Comparison C[2] | Comparison D[3] | Example 4[1] | Comparison C[2] | Comparison D[3] |
| 2 lbs./acre | 90 | 100 | 90 | 70 | 0 | 95 |
| 4 lbs./acre | 100 | 100 | 100 | 100 | 0 | 100 |

[1]Example using 2,6-dichlorobenzylidineaminooxyacetic acid
[2]Comparative example using 3-hydroxy-2,3',4'-trichloroacrylanilide
[3]Comparative example using BASAGRAN
[4]"NR" denotes "not run".

Example 5—Testing of the ethanolamine salt 2,6-dichlorobenzylideneaminooxyacetic acid at various lbs./acre A preferred compound within the scope of the present invention, the ethanolamine salt of 2,6-dichlorobenzylideneaminooxyacetic acid was applied on a preemergence basis and on a postemergence basis to soil containing mixed varieties of undersirable vegetation in the form of seeds or tubers (preemergent) or weed plants (postemergent). The amount applied to the soil were calculated on the basis of the free acid equivalent of 2,6-dichlorobenzylideneaminooxyacetic acid. Approximately three weeks after spray application, the treated areas were examined in comparison with untreated control areas. Results are reported in Table V which follows:

TABLE V

Testing of ethanolamine salt of
2,6-dichlorobenzylideneaminooxyacetic acid

| Weed | Preemergent (lbs./acre) | | | | Postemergent (lbs/acre) | |
|---|---|---|---|---|---|---|
| | ¼ | ½ | 1 | 1½ | 3 | 4 |
| Grasses, percent control | | | | | | |
| Annual rye grass | 50 | 87 | 86 | 98 | 100 | 100 |
| Wild Oats | 57 | 80 | 88 | 98 | 92 | 98 |
| Barnyard grass | NR | 0 | NR | 30 | 0 | 0 |
| Control | 0 | 0 | 0 | 0 | 0 | 0 |
| Broad leaf weeds, percent control | | | | | | |
| Wild mustard | 37 | 77 | 83 | 96 | 69 | 78 |
| Morning glory | NR | 60 | NR | 95 | 60 | 75 |
| Black nightshade | NR | 100 | — | 100 | 100 | 100 |
| Perennials, percent control | | | | | | |
| Yellow nutsedge | 26 | 55 | 81 | 92 | 94 | 99 |
| Purple nutsedge | NR | 38 | 52 | 77 | 84 | 98 |

What is claimed is:

1. A process for the selective control of undesirable vegetation which comprises applying to the locus to be treated a herbicidally effective amount of a compound of the formula:

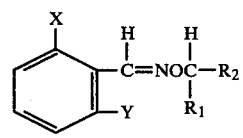

where X and Y are halogen; $R_1$ is hydrogen or $C_1$ to $C_7$ alkyl; and, $R_2$ is selected from the group consisting of a carboxyl group, a metal salt of a carboxyl group, a $C_1$ to $C_{12}$ ester of a carboxyl group, a $C_1$ to $C_4$ alkylamine salt of a carboxyl group, an amide of a carboxyl group, a hydrazid of a carboxyl group, and cyano group.

2. The process of claim 1 wherein said undesirable vegetation is nutsedge.

3. The process of claim 1 wherein said compound is of the formula:

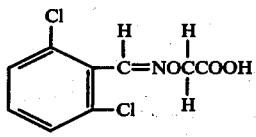

4. The process of claim 1 wherein the locus to be treated contains seeds or tubers of undesirable vegetation.

5. The process of claim 4 wherein the amount of said compound applied to the locus to be treated is between about 1 and about 1.5 lbs./acre.

6. The process of claim 4 wherein said locus contains desirable economic crops, or seeds thereof, selected from the group consisting of corn, soybeans, wheat, cotton, peanuts, rice, and peas.

7. The process of claim 1 wherein the locus to be treated contains undesirable vegetation.

8. The process of claim 7 wherein the amount of said compound applied to the locus to be treated is between about 1.5 and about 4 lbs/acre.

9. The process of claim 7 wherein the amount of said compound is between about 3 and about 4 lbs/acre.

10. The process of claim 7 wherein said locus also contains desirable economic crops selected from the group consisting of wheat, cotton, corn, sorghum, peanuts, peas, rape and rice.

11. A process for providing essentially total vegetative control of weeds in a locus to be treated comprising applying to said locus a compound of the formula:

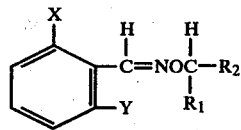

wherein X and Y are halogen; $R_1$ is hydrogen or $C_1$ to $C_7$ alkyl; and $R_2$ is selected from the group consisting of a carboxyl group, a metal salt of a carboxyl group, a $C_1$ to $C_{12}$ ester of a carboxyl group, a $C_1$ to $C_4$ alkylamine salt of a carboxyl group, a hydrazid of a carboxyl group, an amide of a carboxyl group, and a cyano group, in an amount in excess of about 8 lbs./acre.

12. 2,6-dichlorobenzylideneaminooxyacetic acid.

* * * * *